United States Patent
Mueller et al.

(10) Patent No.: US 10,345,250 B2
(45) Date of Patent: Jul. 9, 2019

(54) METHOD OF INSPECTING A SAMPLE WITH A CHARGED PARTICLE BEAM DEVICE, AND CHARGED PARTICLE BEAM DEVICE

(71) Applicant: Applied Materials, Inc., Santa Clara, CA (US)

(72) Inventors: Bernhard G. Mueller, Finsing (DE); Kulpreet Singh Virdi, München (DE); Bernhard Schüler, München (DE); Robert Trauner, Pliening (DE); Ludwig Ledl, Gröbenzell (DE)

(73) Assignee: APPLIED MATERIALS, INC., Santa Clara, CA (US)

( * ) Notice: Subject to any disclaimer, the term of this patent is extended or adjusted under 35 U.S.C. 154(b) by 0 days.

(21) Appl. No.: 15/782,649

(22) Filed: Oct. 12, 2017

(65) Prior Publication Data
US 2019/0113470 A1 Apr. 18, 2019

(51) Int. Cl.
*G01N 23/2251* (2018.01)
*H01J 37/21* (2006.01)
*H01J 37/28* (2006.01)

(52) U.S. Cl.
CPC .......... *G01N 23/2251* (2013.01); *H01J 37/21* (2013.01); *H01J 37/28* (2013.01)

(58) Field of Classification Search
CPC ............ G01N 23/00; G01N 23/20025; G01N 23/203; G01N 23/22; G01N 23/2204; G01N 23/2206; G01N 23/2208; G01N 23/2251; G01N 23/225; H01J 37/00; H01J 37/023; H01J 37/02; H01J 37/26; H01J 37/261

USPC .......................................... 250/306, 307, 311
See application file for complete search history.

(56) References Cited

U.S. PATENT DOCUMENTS

| 4,999,496 A | * | 3/1991 | Shaw | ...................... H01J 37/21 |
| | | | | 250/306 |
| 6,515,296 B1 | * | 2/2003 | Komatsu | ............. G01N 23/225 |
| | | | | 250/559.44 |
| 6,521,891 B1 | * | 2/2003 | Dotan | ..................... H01J 37/21 |
| | | | | 250/307 |

(Continued)

FOREIGN PATENT DOCUMENTS

JP 2007132836 A 5/2007

OTHER PUBLICATIONS

International Search Report, PCT/EP2018/072802 dated Apr. 18, 2019.

*Primary Examiner* — Jason L McCormack
(74) *Attorney, Agent, or Firm* — Patterson + Sheridan LLP

(57) ABSTRACT

A method of inspecting a sample with a charged particle beam device is described. The method comprises arranging the sample on a stage, determining a first focusing strength of an objective lens adapted to focus a charged particle beam on a first surface region of the sample that is arranged at a first distance from the objective lens in a direction of an optical axis, calculating a difference between the first distance and a predetermined working distance based on the determined first focusing strength, adjusting a distance between the first surface region and the objective lens by the calculated difference, and inspecting the first surface region. According to a further aspect, a charged particle beam device configured to be operated according to the above method is described.

19 Claims, 6 Drawing Sheets

(56) References Cited

U.S. PATENT DOCUMENTS

| | | | |
|---|---|---|---|
| 2003/0029998 A1* | 2/2003 | Matsumoto | G01B 15/00 250/307 |
| 2004/0251427 A1* | 12/2004 | Suzuki | H01J 37/20 250/491.1 |
| 2006/0060781 A1 | 3/2006 | Watanabe et al. | |
| 2006/0118719 A1* | 6/2006 | Watanabe | H01J 37/224 250/310 |
| 2009/0140143 A1* | 6/2009 | Fukuda | H01J 37/026 250/311 |
| 2010/0102227 A1* | 4/2010 | Chen | H01J 37/073 250/311 |
| 2010/0193686 A1 | 8/2010 | Watanabe et al. | |

* cited by examiner

METHOD OF INSPECTING A SAMPLE WITH A CHARGED PARTICLE BEAM DEVICE, AND CHARGED PARTICLE BEAM DEVICE

FIELD

The present disclosure relates to a method of inspecting a sample with a charged particle beam device. In particular, a large-area substrate for display manufacturing which may have a non-planar surface is inspected. More particularly, embodiments described herein relate to methods and apparatuses for inspecting samples with a focused charged particle beam, particularly for at least one of imaging, reviewing, inspecting defects, and conducting critical dimension measurements of the sample. Yet further, a charged particle beam device for inspecting a sample is described.

BACKGROUND

In many applications, thin layers are deposited on a substrate, e.g. on a glass substrate. The substrate is typically coated in a vacuum chamber of a coating apparatus. For some applications, the substrate is coated in a vacuum chamber using a vapor deposition technique. Over the last few years, the price of electronic devices and particularly opto-electronic devices has reduced significantly. Further, the pixel density in displays has increased. For TFT displays, a high density TFT integration is beneficial. In spite of the increased number of thin-film transistors (TFT) within a device, the yield is to be increased and the manufacturing costs are to be reduced further.

One or more structures or layers may be deposited on a substrate such as a glass substrate to form an array of electronic or optoelectronic devices such as TFTs on the substrate. A substrate with electronic or optoelectronic structures formed thereon is also referred to as a "sample" herein. During the manufacturing of TFT-displays and other samples, it may be beneficial to inspect one or more structures deposited on the sample to monitor the quality of the sample.

The inspection of the sample can, for example, be carried out by an optical system. However, the dimension of some of the features of the sample or the size of defects to be identified may be below the optical resolution, making some of the defects non-resolvable to the optical system. Charged particles such as electrons may be utilized for inspecting the surface of the sample which may provide a better resolution as compared to optical systems.

However, the inspection of samples with non-planar surfaces with a charged particle beam may be challenging, because not the whole sample surface may be located at the same distance from the objective lens, and the depth of field of a charged particle beam device is limited. Refocusing the charged particle beam modifies the working distance of the device and may introduce beam aberrations and/or measurement errors.

Accordingly, given the increasing demand for an increased quality of displays on large area substrates, there is a need for an improved method for investigating samples with a high measurement accuracy, with reduced beam aberrations, and in a quick and reliable manner. In particular, there is a need for inspecting non-planar large-area samples with a high measurement accuracy, e.g. when conducting critical dimension measurements.

SUMMARY

According to embodiments, methods of inspecting a sample with a charged particle beam device as well as charged particle beam devices for inspecting samples are provided. Further aspects, benefits, and features of the present disclosure are apparent from the claims, the description, and the accompanying drawings.

According to one embodiment, a method of inspecting a sample with a charged particle beam device is provided. The method includes arranging the sample on a stage, determining a first focusing strength of an objective lens adapted to focus a charged particle beam on a first surface region of the sample that is arranged at a first distance from the objective lens in the direction of an optical axis, calculating a difference between the first distance and a predetermined working distance of the charged particle beam device based on the determined first focusing strength, adjusting a distance between the first surface region and the objective lens by the calculated difference, and inspecting the first surface region.

According to another embodiment, a method of inspecting a sample with a charged particle beam device is provided. The method includes arranging the sample on a stage, wherein a sample surface to be inspected and/or a stage surface are non-planar, such that a first surface region of the sample is provided at a first level and a second surface region of the sample that is laterally spaced from the first surface region is provided at a second level, and inspecting both the first surface region and the second surface region at the same predetermined working distance of the charged particle beam device by providing a real-time control of a position of the stage along an optical axis of the charged particle beam device.

According to a further aspect, a charged particle beam device for inspecting a sample is provided. The charged particle beam device includes a stage for arranging a sample to be inspected, an objective lens configured to focus a charged particle beam propagating along an optical axis on the sample, a processing unit configured to determine a first focusing strength of the objective lens adapted to focus the charged particle beam on a first surface region of the sample that is arranged at a first distance from the objective lens in the direction of an optical axis, a calculation unit configured to calculate a difference between the first distance and a predetermined working distance of the charged particle beam device based on the determined first focusing strength, and an adjusting unit configured to adjust a distance between the first surface region and the objective lens by the calculated difference.

Further aspects, advantages and features of the present disclosure are apparent from the description and the accompanying drawings.

BRIEF DESCRIPTION OF THE DRAWINGS

A full and enabling disclosure to one of ordinary skill in the art is set forth in the remainder of the specification including reference to the accompanying drawings wherein.

DETAILED DESCRIPTION

Figure 1:
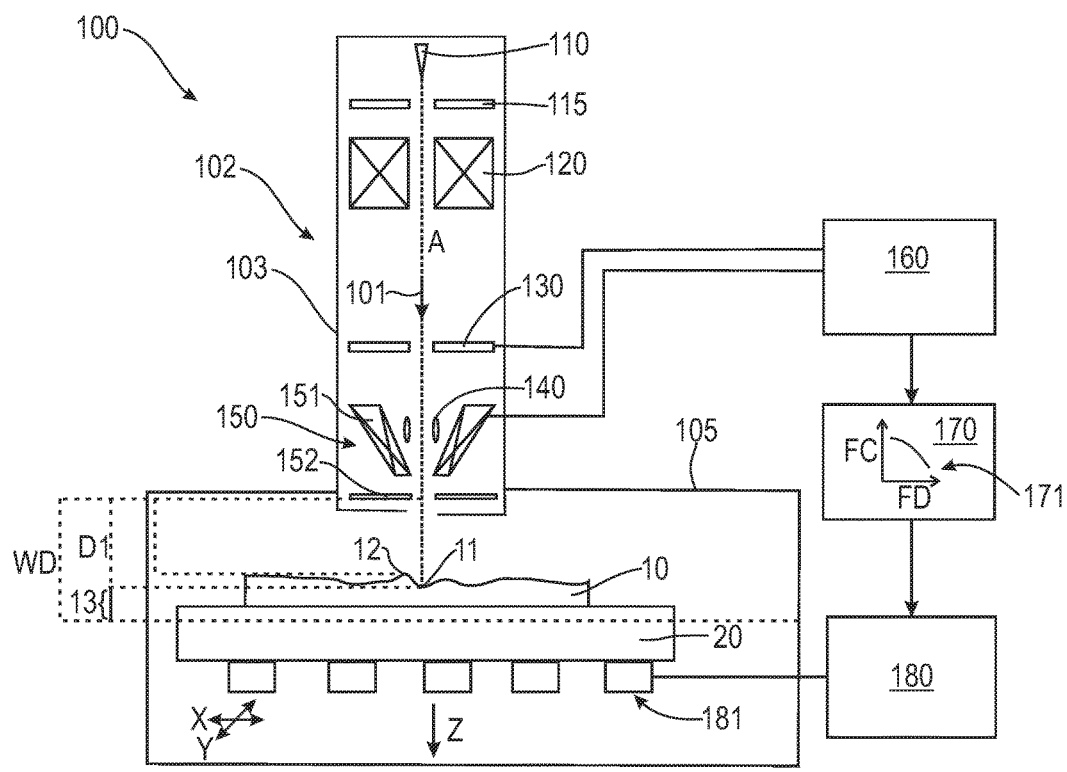
FIG. 1 shows a charged particle beam device configured to be operated according to methods described herein.

Reference will now be made in detail to exemplary embodiments, one or more examples of which are illustrated in the figures. Each example is provided by way of explanation and is not meant as a limitation. For example, features illustrated or described as part of one embodiment can be used on or in conjunction with other embodiments to yield yet further embodiments. The intention is that the present disclosure includes such modifications and variations.

Within the following description of the drawings, same reference numbers refer to same components. Only the differences with respect to the individual embodiments are described. The structures shown in the drawings are not necessarily depicted true to scale but rather serve the better understanding of the embodiments.

FIG. 1 shows a charged particle beam device 100 configured to be operated according to methods described herein. The charged particle beam device 100 may include a scanning electron microscope 102 with a beam source 110 configured to generate a charged particle beam 101, particularly an electron beam. The charged particle beam 101 can be directed along an optical axis A through a column 103 of the scanning electron microscope 102. An inner volume of the column 103 can be evacuated. The scanning electron microscope 102 may include beam influencing elements such as one or more beam deflectors, scan deflectors 140, accelerators 115, decelerators, lens elements 120 or other focusing or defocusing elements, beam correctors, beam separators, detectors and/or further elements provided for influencing the charged particle beam 101 propagating along the optical axis A.

The charged particle beam device 100 includes a stage 20 for arranging a sample 10 to be inspected thereon, and an objective lens 150 configured to focus the charged particle beam on the sample 10 arranged on the stage 20.

The stage 20 may be arranged in a sample inspection chamber 105 which can be evacuated in some embodiments. In some embodiments, the stage 20 may be a movable stage. In particular, the stage 20 may be movable in a plane perpendicular to the optical axis A of the charged particle beam device 100 (also referred to herein as X-Y-plane). By moving the stage 20 in the X-Y-plane, a specified surface region of the sample 10 is moved into an area below the scanning electron microscope 102, such that the specified surface region can be inspected by focusing the charged particle beam 101 thereon. For example, in FIG. 1, a first surface region 11 of the sample 10 is intersected by the optical axis A of the scanning electron microscope 102 such that the first surface region 11 can be inspected. As will be explained in more detail below, the stage 20 may also be movable in the Z-direction, i.e. in the direction of the optical axis A.

According to embodiments described herein, one or more surface regions of the sample 10 are inspected with the charged particle beam device 100. The term "sample" as used herein may relate to a substrate with one or more layers or features formed thereon. The sample may be inspected for one or more of (i) imaging a surface of the sample, (ii) measuring dimensions of one or more features of the sample, e.g. in a lateral direction, i.e. in the X-Y-plane, (iii) conducting critical dimension measurements and/or metrology, (iv) detecting defects, and/or (v) investigating the quality of the sample.

The sample 10 may include an inflexible substrate, e.g., a glass substrate or a glass plate, or a flexible substrate, such as a web or a foil. The sample may be a coated substrate, wherein one or more thin material layers or other features are deposited on the substrate, for example by a physical vapor deposition (PVD) process or a chemical vapor deposition process (CVD). In particular, the sample may be a substrate for display manufacturing having a plurality of electronic or optoelectronic devices formed thereon. The electronic or optoelectronic devices formed on the substrate are typically thin film devices including a stack of thin layers. For example, the sample may be a substrate with an array of thin film transistors (TFTs) formed thereon, e.g. a thin film transistor based substrate.

Embodiments described herein particularly relate to the inspection of a sample, wherein the sample includes a structure formed on a substrate. In some embodiments, the structure may be formed by lithography and/or etching. The structure may include electronic or optoelectronic devices such as transistors, particularly thin film transistors. The sample may include a large area substrate, particularly a large area substrate for display manufacturing, e.g. having a surface area of 1 m² or more.

In some embodiments, a surface of the sample to be inspected may be a non-planar surface. For example, the sample surface may be rough, uneven or may include 3-dimensional features or structures having a varying height formed thereon. As is schematically depicted in FIG. 1, the sample 10 may include a first surface region 11 that is provided at a first level and a second surface region 12 laterally spaced from the first surface region 11 that is provided at a second level. In other words, the height of the first surface region 11 differs from the height of the second surface region 12 relative to a plane of the objective lens 150.

In some embodiments, the sample (which may have a planar or a non-planar sample surface) may be arranged on the stage 20, wherein the stage 20 has a non-planar stage surface. Accordingly, when the sample 10 is arranged on the non-planar stage surface, the sample has a first surface region 11 and a second surface region 12 which are arranged at different levels. The "level" of a surface region of a sample that is arranged on the stage may refer to a height of the surface region in the direction of the optical axis A, i.e. relative to a plane of the objective lens 150.

According to some embodiments, the sample may include a large-area substrate having a size of at least 1 m². The size may be from about 1.375 m² (1100 mm×1250 mm—GEN 5) to about 9 m², more specifically from about 2 m² to about 9 m² or even up to 12 m². For instance, a substrate can be GEN 7.5, which corresponds to a surface area of about 4.39 m² (1.95 m×2.25 m), GEN 8.5, which corresponds to a surface area of about 5.7 m² (2.2 m×2.5 m), or even GEN 10, which corresponds to a surface area of about 9 m² (2.88 m×3130 m). Even larger generations such as GEN 11 and GEN 12 can be implemented.

For inspecting a sample with the charged particle beam 101, the charged particle beam is typically focused on the sample surface with the objective lens 150. Secondary electrons or backscattered electrons (also referred to as "signal electrons") are generated when the charged particle beam 101 impinges on the sample surface. The signal electrons provide information on spatial characteristics and dimensions of features of the sample surface and are detected with a detector 130. By scanning the charged particle beam 101 over the sample surface, e.g. with scan deflectors 140, and detecting the signal electrons as a function of generation position of the signal electrons, the sample surface or a portion thereof can be imaged.

In some embodiments, one or more scan deflectors 140 may be provided for scanning the charged particle beam 101 over the surface of the sample, e.g. in the X-direction and/or in the Y-direction.

A small spot of the focused charged particle beam on the sample surface increases the obtainable image resolution. Accordingly, the sample surface should be arranged in the plane of focus of the objective lens during inspection. The distance between the downstream end of the objective lens 150 and the plane of focus of the charged particle beam where the sample surface is to be arranged is typically referred to as the "working distance" of the charged particle beam device 100.

Inspecting a non-planar sample surface with a charged particle beam may be challenging because not all surface regions lie within a common plane of focus. Upwardly protruding surface regions cannot be sharply imaged without locally adapting the focusing strength of the objective lens. The focusing strength of the objective lens may be adapted depending on a local height of the surface region to be inspected, e.g. by utilizing an autofocusing process. For example, the objective lens may include a magnetic lens component 151 with one or more coils. The focusing strength of the objective lens may be increased by increasing the focusing current FC which is applied to the one or more coils of the magnetic lens component 151 (decreasing the focusing distance FD), and the focusing strength of the objective lens may be decreased by decreasing the focusing current FC applied to the one or more coils (increasing the focusing distance FD). The focusing distance FD may be understood as the distance between the downstream end of the objective lens and the plane of focus when exciting the objective lens with an associated focusing current FC.

Figure 3:
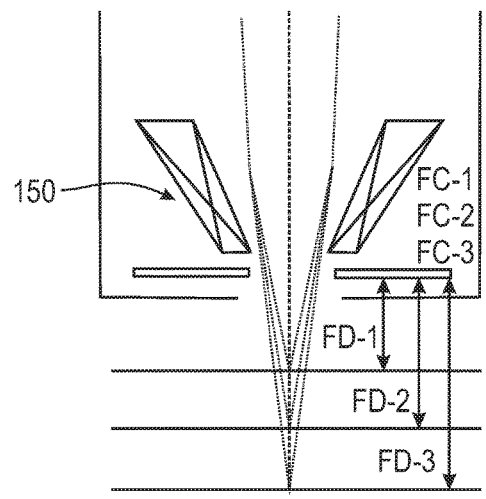
FIG. 3 shows a schematic view of an objective lens for illustrating the dependency of the focusing distance on the focusing strength.

FIG. 3 illustrates three different focusing distances FD-1, FD-2, FD-3 of an objective lens 150 that is operated at three different focusing strengths (focusing currents FC-1, FC-2, FC-3). By adjusting the focusing current FC of the objective lens, the plane of focus can be shifted toward or away from the objective lens 150. Samples having a varying surface level can be sharply imaged by locally adjusting the focusing current FC of the objective lens. In other words, when an uneven sample surface or a sample that is arranged on a non-planar stage is to be inspected, the focusing current of the objective lens 150 may be changed depending on the level of the surface region to be inspected.

However, a change of the focusing current FC of the objective lens 150 for focusing the charged particle beam 101 on the surface region to be inspected leads to a change in the pixel size (nm/pixel), the scan amplitude staying the same. In particular, the calibrations performed during the start-up or service of the charged particle beam device 100 are valid only for a certain range of focusing strength. A strong variation of the focusing strength of the objective lens due to an unevenness of the sample surface therefore negatively affects the measurement accuracy.

Figure 4A:
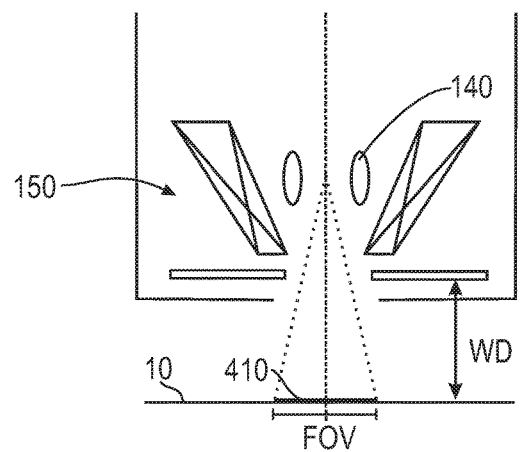
FIGS. 4A and 4B illustrate the dependency of the field of view on the working distance of a charged particle beam device.
Figure 4B:
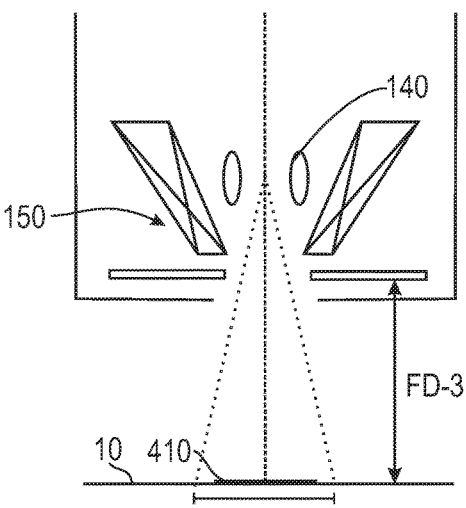

FIGS. 4A and 4B illustrate the negative impact of a varying focusing strength on the measurement accuracy. For calibrating a charged particle beam device, a calibration object with one or more known dimensions is placed at a predetermined working distance WD from the objective lens 150 which corresponds to a predetermined focusing strength of the objective lens 150. In other words, the calibrations are typically performed in a predetermined plane of focus. A given scan current of a scan deflector 140 is applied for imaging the calibration object with the known dimension. Using the correlation with the size of this known calibration object located at the predetermined working distance WD, allows for calculating the scan current corresponding to a given size of the image, also known as the "field of view" (FOV). Accordingly, the scan current appropriate for any given FOV can be determined.

When the height of a non-planar sample changes by an unknown value, and a FOV is chosen to image the sample, inaccuracies arise. In particular, the used scan current results in a FOV which is not the actual FOV of a region of the sample which does not lie in the predetermined plane of focus where the calibration was performed.

For example, FIG. 4A shows a sample 10 which is arranged in the predetermined plane of focus where the calibration was performed. In other words, the surface of the sample 10 of FIG. 4A is arranged at the predetermined working distance WD relative to the objective lens 150. Accordingly, the correlation between the scan current and the FOV is known and the actual dimension of a feature 410 of the sample can be measured.

FIG. 4B shows a sample 10 which is arranged in a more distant plane such that the focusing distance FD-3 between a surface region of the sample 10 and the objective lens is larger than the predetermined working distance WD. Accordingly, the feature 410 of the sample 10 appears smaller than the actual dimension of the feature 410. Similarly, when the distance between a surface region of the sample to be inspected and the objective lens is smaller than the predetermined working distance, a feature of the sample appears bigger than the dimension of the actual structure.

In this context, it is noted that for a charged particle beam with a high landing energy on the sample, the above-described measurement error may be comparably low. However, when using a charged particle beam with a low landing energy, the measurement error may become significant, e.g. in case of an electron beam with a landing energy of 1 keV or less. Accordingly, measurement errors may become significant in the case of a charged particle beam device including a low voltage SEM (LV-SEM).

Low energy electron beams are beneficial for the inspection of glass samples or other non-conductive samples. However, low-energy electron beams are more sensitive to height variations of the sample surface.

Conventional methods of determining an appropriate positioning of the sample to be inspected cannot determine the appropriate positioning of the sample to the level of accuracy as appropriate for the inspection of large area substrates such as glass substrates as used for the manufacture of flat panel and/or TFT based displays.

According to the methods described herein, the point of focus of a charged particle beam device can be accurately controlled such that the sample surface to be investigated stays close to the predetermined plane of focus where the calibration measurements were previously performed. The charged particle beam device can, therefore, be operated with a high accuracy and reduced measurement errors.

Now returning to FIG. 1, the method of inspecting the sample 10 described herein includes arranging the sample 10 on the stage 20. The sample 10 includes a first surface region 11 that is to be inspected with the charged particle beam device 100. The first surface region 11 is arranged at an (initially unknown) first distance D1 from the objective lens 150. Since the first distance D1 from the objective lens 150 to the first surface region 11 is not initially known, the first surface region 11 may not be positioned in a plane of focus of the objective lens. Further, the first surface region 11 may not be positioned at the predetermined working distance WD from the objective lens 150.

According to the method described herein, a first focusing strength of the objective lens 150 is determined that is adapted to focus the charged particle beam 101 on the first surface region 11 of the sample. For example, the objective lens 150 may be excited with varying focusing currents FC and various images may be acquired. The various images may be investigated and the focusing current FC which generates the image with the best focus among the various images may be determined as the first focusing strength.

In some implementations, the first focusing strength of the objective lens 150 may be determined with an autofocusing process.

It is noted that a sharp image of the first surface region 11 may be obtainable by focusing the charged particle beam 101 on the first surface region 11 with the first focusing strength. However, the first surface region 11 is not arranged at the predetermined working distance WD where the calibration measurements were previously performed. Accordingly, dimensional values of the first surface region 11 cannot be accurately measured and metrology cannot be accurately performed when the first surface region 11 is arranged at the first distance D1.

Subsequently, a difference 13 between the first distance D1 and the predetermined working distance WD is calculated based on the determined first focusing strength. FIG. 1 schematically shows a calculation unit 170 which may receive the first focusing strength as an input parameter from a processing unit 160 and may provide the difference 13 as an output parameter.

The distance between the first surface region 11 and the objective lens 150 is then adjusted by the calculated difference 13. After adjusting the distance, the first surface region 11 is essentially arranged at the predetermined working distance WD from the objective lens 150 where the calibration measurements were previously performed. Accordingly, accurate measurements of dimensions of the sample surface can be conducted. FIG. 1 schematically shows an adjusting unit 180 which receives the calculated difference 13 and adjusts the distance between the first surface region 11 and the objective lens 150, e.g. by moving the stage 20 in the direction of the optical axis A.

Figure 2:
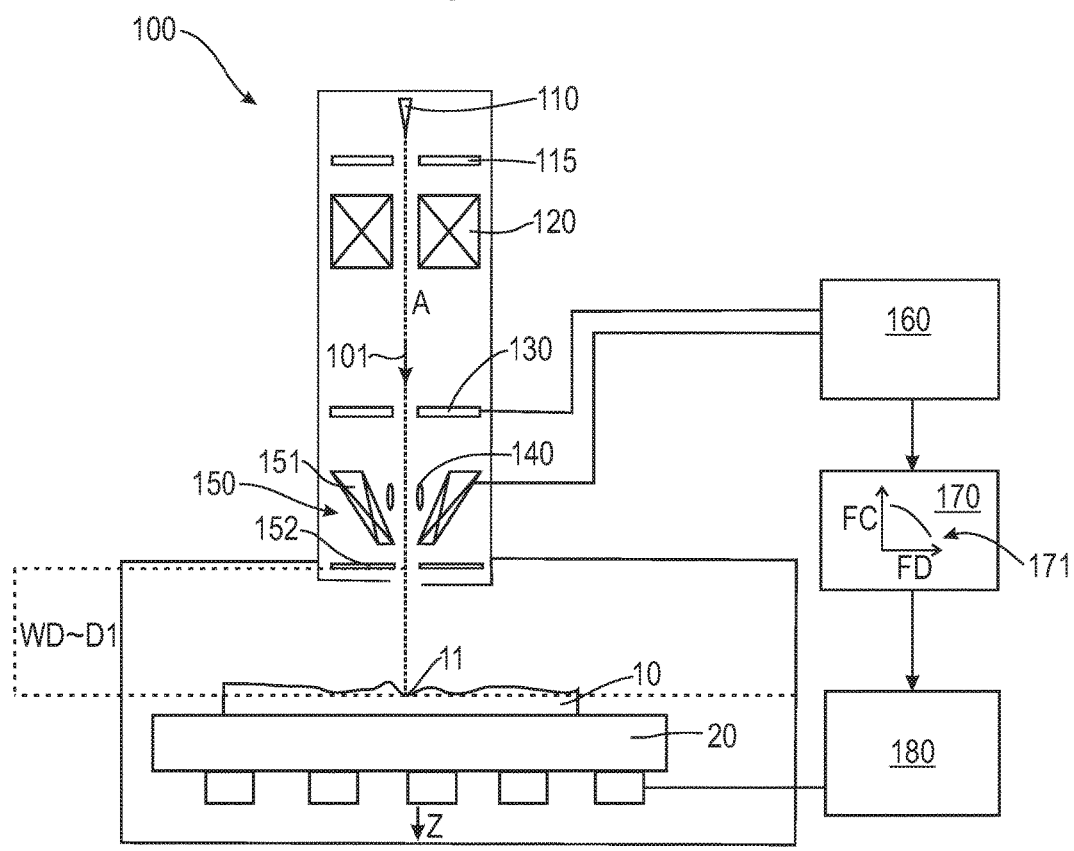
FIG. 2 shows the charged particle beam device of FIG. 1 in a state for inspection of the sample.

FIG. 2 schematically shows the charged particle beam device 100 of FIG. 1 in a state for inspecting the first surface region 11. The distance between the first surface region 11 and the objective lens 150 has been adjusted by the calculated difference 13 such that the first surface region 11 is arranged at the predetermined working distance WD from the objective lens. In particular, the stage 20 has moved in a downward direction away from the objective lens 150 by the calculated difference 13.

After adjusting the distance between the first surface region 11 and the objective lens 150 by the calculated difference 13, the first surface region 11 is inspected. For example, critical dimension measurements and metrology can be performed and/or the first surface region 11 can be imaged. It is to be noted that the correlation between the scan current of the scan deflector 140 and the field of view FOV is more accurate when the first surface region 11 is essentially arranged at the predetermined working distance WD from the objective lens 150.

In some implementations, the distance between the first surface region 11 and the objective lens 150 is adjusted by moving the stage 20 in the direction of the optical axis A by the calculated difference 13. In particular, the stage 20 may be movable in the direction of the optical axis A (also referred to herein as a Z-direction), i.e. away from the objective lens 150 and/or toward the objective lens 150. By moving the stage 20 having the sample 10 positioned thereon in the Z-direction by the calculated difference 13, the first surface region 11 is moved to the predetermined plane of focus that is arranged at the predetermined working distance WD from the objective lens 150. A stage movement system for moving the stage 20 in the Z-direction may be provided. As already mentioned above, the stage 20 may additionally be movable in the X-Y-plane perpendicular to the optical axis A.

The method according to embodiments described herein may be performed in real time, i.e. during the inspection of a sample 10 with a previously unknown surface roughness or non-planarity. Further, it is not necessary to previously know about potential imprecisions of the stage movement system and/or to specifically consider displacements of components due to pressure changes between the sample inspection chamber 105 and the outside atmosphere in which the charged particle beam device 100 is located. For example, a change of pressure gradient between the sample inspection chamber 105 and the atmosphere may cause the top surface of the sample inspection chamber 105 on which the column 103 is mounted to move downward during evacuation. Such factors do not negatively influence the measurement results obtained according to the described method because the measurements are always conducted essentially at the predetermined working distance WD.

According to embodiments, which may be combined with other embodiments described herein, the first focusing strength of the objective lens 150 is determined by an autofocusing process. An autofocusing process can be conducted in a quick and reliable manner.

In some embodiments, the autofocusing process includes imaging the first surface region 11 with varying focusing strengths of the objective lens 150 and analyzing an image sharpness or an image contrast. For example, the focusing current of the objective lens 150 may be stepwise increased (or stepwise decreased) as long as the image quality (e.g. the image sharpness or the image contrast) of the respectively obtained image improves. The focusing current that leads to an image with a maximum image quality corresponds to the first focusing strength that is adapted to focus the charged particle beam on the first surface region.

In some embodiments, which may be combined with other embodiments described herein, the difference 13 between the first distance D1 and the predetermined working distance WD is calculated based on the determined first focusing strength and using a previously obtained table or function 171 which relates focusing strengths of the objective lens 150 to the respective focusing distances FD.

It is noted that, assuming a given working point of the device, each focusing strength of the objective lens, i.e. each focusing current FC applied to the one or more coils of the objective lens 150, relates to a corresponding focusing distance FD of the objective lens 150. In other words, the focusing distance FD is a monotonic function of the focusing current FC. A given relationship between the focusing distance FD and the focusing current FC holds true for a given working point of the device. When the working point changes, for example by varying the energy of the charged particle beam or by varying the column energy, the relationship between the focusing distance FD and the focusing current FC of the objective lens 150 changes as well. For a different set of conditions (especially including a different beam energy) an associated relationship between FD and FC exists. For example, the shape of the function may be similar for a different set of conditions, but the magnitude may change. Accordingly, the table or function 171 is not universal for a given objective lens 150.

The relation between the focusing strength and the focusing distance can be previously determined, e.g. on an appropriate test location and setting a specified working point, by varying the focusing distance FD in steps, e.g. by utilizing a calibration object having a plurality of regions arranged on known levels. A table or function 171 can be created that assigns a plurality of focusing strengths to corresponding focusing distances FD. By interpolation, the focusing distance FD as a monotonic function of the focusing current FC can be obtained at the specified working point. FIG. 1 schematically shows a calculation unit 170 including a memory where the focusing current as a monotonic function of the focusing distance FD is stored, e.g. in the form of a table or function 171. In reality, said monotonic function is an essentially linear function in a region close to the working distance WD that is of interest for the present application.

Figure 5:
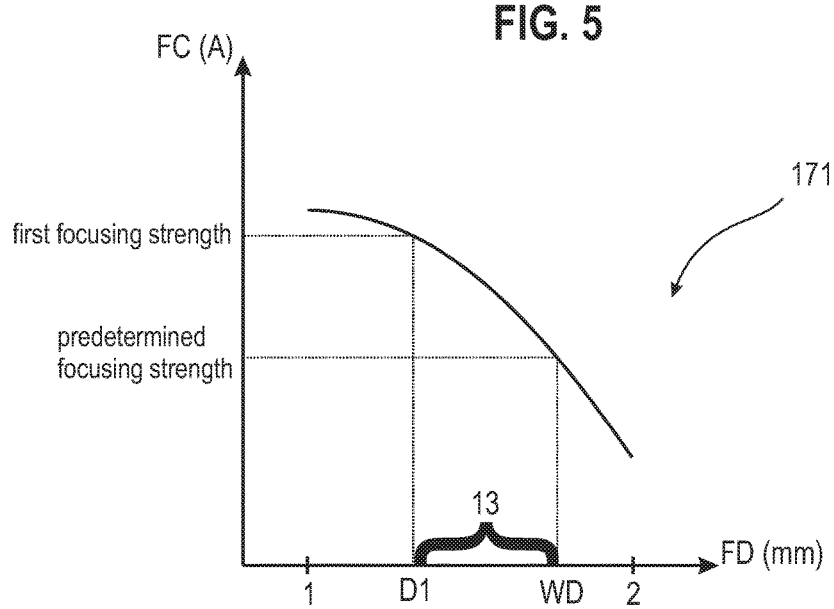
FIG. 5 is a schematic illustration of a table or function relating focusing strengths to focusing distances of the objective lens.

FIG. 5 is a schematic view of the table or function 171 that can be used for calculating the difference 13 between the predetermined working distance WD and the (initially unknown) first distance D1 based on the determined first focusing strength. The function shows the focusing strength depending on the focusing distance FD in an (exemplary) region between 1 mm and 2 mm from the objective lens. The focusing strength is expressed in terms of the focusing current FC (in Ampere) to be applied to one or more coils of a magnetic lens component 151 of the objective lens 150 adapted to obtain a corresponding focusing distance. It is clearly shown in FIG. 5 that, based on the determined first focusing strength, the difference 13 can be calculated, e.g. by previously interpolating the values stored in a respective table.

For example, the table may include a plurality of focusing distances FD in the range between 1 mm and 5 mm, particularly in the range between 1 mm and 2 mm, and the corresponding focusing strengths, which may be expressed in terms of the focusing current FC to be applied to the objective lens at a specified working point.

In implementations, prior to the inspection of a sample, a calibration object having a structure including a plurality of levels with known level heights may be inspected and the corresponding focusing currents FC of the objective lens may be obtained. One of these levels may be provided at the predetermined working distance WD from the objective lens such that the table also contains a value of the predetermined focusing strength that corresponds to the predetermined working distance WD. Alternatively, the predetermined focusing strength corresponding to the predetermined working distance WD can be obtained by interpolation of the actually measured values.

Having determined the first focusing strength and utilizing said table or function 171, the difference 13 between the first distance D1 and the predetermined working distance WD can be calculated based on the determined first focusing strength, as is schematically indicated in FIG. 5.

In some embodiments, which may be combined with other embodiments described herein, the distance between the first surface region 11 and the objective lens 150 may be adjusted in an iterative process, before the first surface region 11 is inspected.

In particular, after adjusting the distance between the first surface region 11 and the objective lens 150 by the calculated difference 13, the first surface region 11 may still not be arranged exactly at the predetermined working distance WD, e.g. due to imprecisions of the stage movement system which may not move the stage exactly by the calculated difference.

Figure 6:
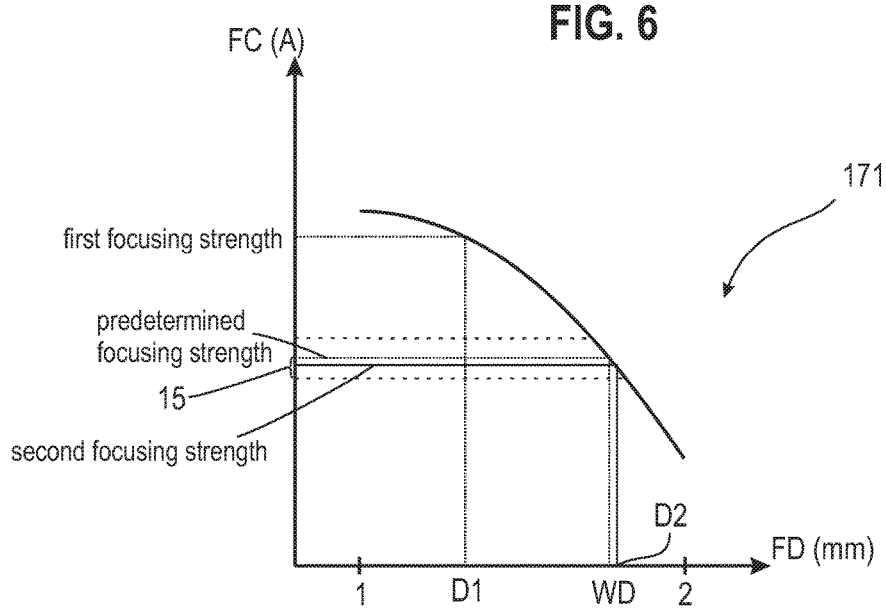
FIG. 6 is a schematic illustration of a table or function relating focusing strengths to focusing distances of the objective lens.

For example, as is schematically illustrated in FIG. 6, after adjusting the distance, the first surface region 11 may be arranged at a second distance D2 close to the predetermined working distance WD, but not exactly at the predetermined working distance WD. For example, the stage 20 may have moved slightly too far, e.g. due to mechanical tolerances. Accordingly, it may be reasonable to adjust the position of the stage in an iterative process, wherein each iteration may move the first surface region 11 of the sample 10 closer to the predetermined focusing plane arranged at the predetermined working distance WD from the objective lens.

In some implementations, after adjusting the distance between the first surface region 11 and the objective lens 150 by moving the stage 20 by the calculated difference 13, it may be determined (e.g., utilizing the table or function 171) whether indeed now the focusing strength of the objective lens that focuses the charged particle beam on the first surface region 11 essentially corresponds to the predetermined working distance WD. Thus, a second focusing strength of the objective lens may be determined that is adapted to focus the charged particle beam on the first surface region 11, e.g. by using the above mentioned auto-focusing process. It may then be calculated (e.g., again utilizing the table or function 171) whether a difference between the second focusing strength and the predetermined focusing strength is smaller than a predetermined threshold value 15. The predetermined focusing strength is the focusing strength of the objective lens that focuses the charged particle beam on a sample surface arranged at the predetermined working distance WD.

In the case of a positive calculation result, the method may continue with the inspection of the first surface region 11. In the example that is illustrated in FIG. 6, the first surface region 11 is arranged close enough to the predetermined working distance WD such that the difference between the second focusing strength and the predetermined focusing strength is smaller than the predetermined threshold value 15. Accordingly, the calculation would lead to a positive result and the method would continue with the inspection of the first surface region 11.

In the case of a negative calculation result, the iterative process may continue, until the first surface region 11 is arranged close enough to the working distance WD such that an inspection of the sample with a requested measurement accuracy is possible. In the case of a continuation of the iterative process, the stage may be moved a second time by a second calculated difference in the direction of the optical axis A, in order to bring the first surface region 11 closer to the predetermined working distance WD.

In some embodiments, the predetermined threshold value 15 may be set such that an inspection of the sample with a requested measurement accuracy is enabled when the second focusing strength does not deviate from the predetermined focusing strength by more than the predetermined threshold value 15.

In some implementations, which may be combined with other implementations described herein, a requested measurement accuracy may be pre-specified. For example, an allowable measurement error may be decided on according to accuracy demands of a specific measurement to be conducted or of the specific situation and application. For example, a maximum relative measurement error (in %) may be pre-specified or a maximum absolute measurement error in nm for a given field of view (FOV) may be pre-specified. In an example, the measured dimension of a feature having an actual dimension of 200 nm should not be 198 nm or less or 202 nm or more (corresponding to a maximum relative measurement error of about 1%). Then, the corresponding range of focusing strength around the predetermined focusing strength can be determined such that the measurement accuracy for imaging an object with a given FOV and image size is always better than the requested accuracy. The predetermined threshold value 15 whose exceedance leads to a further iteration of the iterative process can be determined from said range of focusing strength (e.g., expressed in terms of focusing current FC).

Summarizing the above, the predetermined threshold value 15 may be determined such that, in the case of a positive calculation result, the first surface region 11 is arranged close enough to the predetermined working distance WD for being inspected with a measurement accuracy better than or equal to the pre-specified measurement accuracy.

According to some embodiments, which may be combined with other embodiments described herein, the charged particle beam device may be previously calibrated. The calibration may include: arranging a scan object with one or more known lateral dimensions at the predetermined working distance WD, and determining a relation between at least one scan current of a scan deflector 140 and at least one lateral dimension of the scan object. By calibrating the charged particle beam device 100 utilizing a scan object arranged at the predetermined working distance WD, highly accurate measurements can in turn be conducted on sample regions which are arranged close to or exactly at the predetermined working distance WD. Methods described herein provide for an automated arrangement of sample regions arranged at initially unknown levels essentially or exactly at the predetermined working distance WD from the objective lens 150, allowing for highly accurate and reliable measurements and metrology of the sample.

In some implementations, the charged particle beam device 100 may be previously adjusted with view to an inspection of an object that is arranged at the predetermined working distance WD. In particular, the working point WP of the charged particle beam device 100 may be set such that high-accuracy measurements can be conducted on an object arranged at the predetermined working distance WD. For example, previously adjusting the charged particle beam device may include one or more of: setting a beam energy, setting a landing energy of the charged particle beam, aligning one or more beam deflectors, aligning one or more scan deflectors, aligning one or more accelerators or decelerators, aligning one or more beam aberration correctors, and/or aligning the objective lens. The working point settings may include appropriate alignment settings of beam influencing devices for the beam to propagate along the optical axis A with reduced aberrations like chromatic aberration, spherical aberration, skew and/or stigmation. At the working point settings, an aberration-minimized beam may be focused with the predetermined focusing strength to the predetermined plane of focus that is located at the predetermined working distance WD.

In particular, the working point WP of the charged particle beam device may be set such that aberration-minimized and highly accurate measurements are possible on a sample surface that is arranged at the predetermined working distance WD.

In some embodiments, which may be combined with other embodiments described herein, the charged particle beam 101 impinges on the sample with a landing energy of 5 keV or less, particularly 1 keV or less. For example, the objective lens 150 may include a retarding field component 152 configured to decelerate the charged particle beam 101 to a landing energy of 5 keV or less. The retarding field component may include a retarding electrode. In particular, the charged particle beam device 100 may include a low voltage SEM (LV-SEM).

Low energy charged particle beams, particularly low-energy electron beams, do not penetrate deeply into the sample and may therefore provide superior high-quality information about the features on the sample surface. In particular, an advantage of having a landing energy of 5 keV or below, particularly a landing energy of 2 keV or below, is that the electron beam impinging onto the sample generates a stronger signal compared to high-energy electron beams. Since layers, e.g. LTPS layers, deposited on the substrate are thin and since high-energy electrons penetrate deeper into the sample, i.e. below the layer, only a few high-energy electrons may generate a detector signal that contains information about the surface layer. In contrast, low-energy electrons, such as electrons having a landing energy of 2 keV or 1 keV or below, penetrate into a shallow region of the sample only and thus provide more information about the surface layer. Accordingly, an improved image of e.g. grain boundaries may be provided even when, as provided by embodiments described herein, no surface etching of the substrate is carried out.

However, the lower the landing energy of the charged particle beam, typically the smaller the allowable tolerance with is respect to a varying focusing current of the objective lens during inspection. This is because, for low-energy particles, already a small variation of the focusing current FC may lead to substantial measurement errors, as is schematically indicated in FIG. 4B.

According to embodiments, which may be combined with other embodiments described herein, a plurality of surface regions of the sample 10 may be subsequently imaged. For example, the first surface region 11 of the sample 10 of FIG. 1 is inspected first, and the second surface region 12 of the sample 10 that has a higher level is inspected afterwards. The surface profile of the sample 10 may not be previously known such that, in order to obtain high-accuracy measurements, the stage position may need to be adjusted in real time, in the course of a partially or entirely automated measurement program, before the inspection of each of the plurality of surface regions.

The inspection of each surface region of the plurality of surface regions may include: determining a respective focusing strength adapted to focus the charged particle beam 101 on the respective surface region that is arranged at a respective (initially unknown) distance from the objective lens, calculating a difference between the respective distance and the predetermined working distance WD based on the respective focusing strength, and adjusting a distance between the respective surface region and the objective lens 150 by moving the stage 20 by the calculated difference in the direction of the optical axis A. Optionally, for each surface region to be inspected, the distance between the respective surface region and the objective lens is adjusted in an iterative manner, until the respective surface region is arranged close enough to the predetermined working distance. A pre-specified measurement accuracy can be provided.

In other words, before inspecting a respective surface region of a plurality of surface regions to be inspected, the stage is moved in the direction of the optical axis such that the respective surface region is arranged close to or essentially at the predetermined working distance WD from the objective lens. The calibration measurements of the charged particle beam device may have been previously performed in a plane of focus extending at the predetermined working distance WD.

Further, the working point WP of the charged particle beam device may have been previously adjusted with view to measurements to be performed on a sample arranged at the predetermined working distance WD. The working point settings may include adjusting one or more beam influencing components such that an aberration-reduced beam focus at the predetermined working distance WD can be provided. Accordingly, each surface region can be inspected with a high accuracy and with reduced aberrations.

In some embodiments, which may be combined with other embodiments described herein, the first surface region 11 and a second surface region 12 of the sample 10 which is laterally spaced-apart from the first surface region 11 are located at different levels in the direction of the optical axis A, i.e. at different heights. The method includes successively inspecting the first surface region 11 and the second surface region 12 at the predetermined working distance WD by providing a real-time control of a position of the stage 20 along the optical axis A.

A "real-time control" as used herein may be understood as a control of the position of the stage during a partially or entirely automated measurement process enabling an inspection of a plurality of laterally spaced surface regions of the sample at the predetermined working distance. In particular, the stage position in the Z-direction may be automatically controlled such that the first surface region 11 and the second surface region 12 are both inspected while being located at the predetermined working distance WD from the objective lens. An on-axis control may be provided, i.e. the distance between the sample surface to be inspected and the objective lens may be checked and controlled along the optical axis A.

According to a further aspect described herein, a method of inspecting a sample 10 with a charged particle beam device 100 is described. The method includes arranging the sample 10 on a stage 20, wherein a sample surface to be inspected and/or a stage surface are non-planar, such that a first surface region 11 of the sample is provided at a first level and a second surface region 12 of the sample is provided at a second level with respect to an optical axis A of the charged particle beam device. The first surface region 11 and the second surface region 12 are successively inspected while being arranged at the same predetermined working distance WD from an objective lens 150 of the charged particle beam device 100. For arranging both the first surface region and the second surface region at the predetermined working distance WD, the position of the stage 20 along the optical axis is controlled in real-time in the course of a respective measurement process.

The method may include some or all features of the methods described above, such that reference can be made to the above explanations which are not repeated here.

In particular, the method may include determining a first focusing strength of the objective lens adapted to focus the charged particle beam on the first surface region, calculating a difference between the first distance and the predetermined working distance WD based on the determined first focusing strength, moving the stage 20 along the optical axis by the calculated difference, and inspecting the first surface region. Then, the sample may be moved in a lateral direction until the second surface region 12 can be inspected with the charged particle beam 101. However, the second surface region 12 is not yet arranged at the predetermined working distance WD from the objective lens 150. Accordingly, the method may further include determining a focusing strength of the objective lens adapted to focus the charged particle beam on the second surface region, calculating a difference between said distance and the predetermined working distance WD based on said determined focusing strength, moving the stage 20 along the optical axis by said calculated difference, and inspecting the second surface region. The second surface region can be inspected with a high measurement accuracy because the second surface region is arranged essentially at the predetermined working distance from the objective lens. As explained above, it is optionally possible to implement an iterative process, wherein each iteration may bring the respective surface region closer to the predetermined working distance WD.

FIG. 1 and FIG. 2 show a charged particle beam device 100 for inspecting a sample according to embodiments described herein in a schematic view. The charged particle beam device includes a stage 20 for arranging a sample to be inspected, and an objective lens 150 configured to focus a charged particle beam 101 propagating along an optical axis A on the sample 10. The charged particle beam device 100 further includes a processing unit 160, a calculation unit 170, and an adjusting unit 180.

The processing unit 160 is configured to determine a first focusing strength of the objective lens 150 adapted to focus the charged particle beam 101 on the first surface region 11 of a sample 10 that is arranged at a first distance D1 from the objective lens 150 in the direction of the optical axis A. In some implementation, the processing unit 160 may include an image acquisition and analyzing unit, particularly an autofocusing device. The processing unit 160 may be connected to the objective lens 150 and to a detector 130 of the charged particle beam device 100. Accordingly, the focusing current FC of the objective lens may be controlled. The processing unit 160 may obtain images of the first surface region 11 at varying focusing strengths of the objective lens 150 and may analyze the obtained images. The focusing current FC utilized for obtaining an image with a maximum image sharpness or image contrast corresponds to the first focusing strength adapted to focus the charged particle beam on the first surface region 11.

The calculation unit 170 may be configured to calculate a difference 13 between the first distance D1 and the predetermined working distance WD on the basis of the determined first focusing strength. In some implementations, the calculation unit may include a memory or may have access to a memory, wherein a table or a function 171 is stored in the memory. The table or function may relate focusing strengths of the objective lens to respective focusing distances FD. For example, as is schematically depicted in FIG. 1 and FIG. 2, the table or function 171 may assign a plurality of focusing currents FC of the objective lens to respective focusing distances FD of the objective lens 150. One entry of said table or function may assign a predetermined focusing strength of the objective lens to the predetermined working distance WD. Based on the first focusing distance and utilizing said table or function 171, the difference between the first distance D1 and the working distance WD can be calculated.

Said table or function 171 may be obtained and saved in the memory in the course of a previously conducted calibration, e.g. by utilizing a calibration object having a plurality of regions arranged at known levels or heights. Alternatively, the table or function 171 may be obtained from another source and stored in a memory of the charged particle beam device 100.

The adjusting unit 180 may be configured to adjust a distance between the first surface region 11 and the objective lens 150 by the calculated difference 13. In some implementations, the adjusting unit 180 includes a stage motion controller 181 configured to move the stage 20 in the direction of the optical axis A, i.e. in the Z-direction. In some embodiments, the stage 20 may further be movable in the X-Y-plane, i.e. perpendicular to the optical axis A.

In some embodiments, the objective lens 150 may include a retarding field component 152 configured to decelerate the charged particle beam 101 to a landing energy of 5 keV or less, particularly 2 keV or less, more particularly 1 keV or less, or even 500 eV or less.

The stage 20 may be configured for supporting a large-area substrate for display manufacturing, particularly having a size of 1 m² or more. In particular, the stage 20 may have a stage surface for supporting a sample with a surface area of 1 m² or more. Large stage surfaces are typically not perfectly planar. For example, the stage surface may have local deviations from a perfectly planar surface in the range of several tens of microns. When a large-area sample is placed on the stage surface, the non-planarity of the substrate support surface may affect the height structure of the sample surface. For example, the non-planarity of a sample may increase by placing the sample on the stage. According to methods described herein, accurate dimensional measurements can be conducted for planar or non-planar samples even if placed on a not perfectly planar stage surface of a stage 20.

Large-area samples having a surface area of 1 m² or more, particularly 2 m² or more can be inspected with the charged particle beam device 100 described herein.

In some embodiments, which may be combined with other embodiments described herein, the charged particle beam device 100 may further include a control unit configured to control the adjusting unit 180 to adjust the distance between the first surface region 11 and the objective lens 150 in an iterative process, wherein the first surface region 11 is brought closer to the predetermined working distance WD during each successive iteration.

Figure 7:
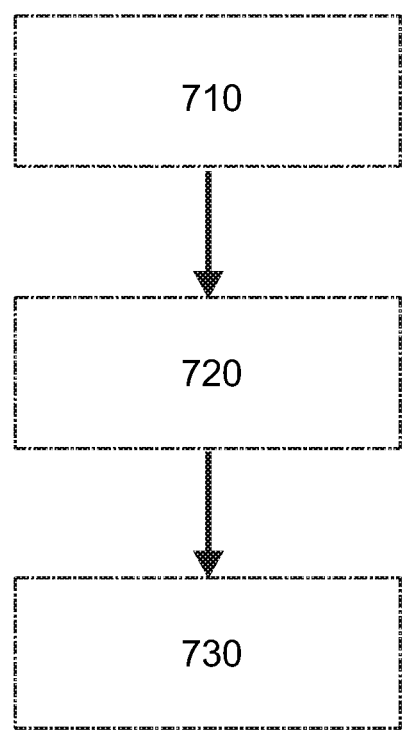
FIG. 7 is a flow diagram illustrating a method of inspecting a sample according to embodiments described herein.

FIG. 7 is a flow diagram for illustrating a method of inspecting a sample according to embodiments described herein.

In (optional) box 710, a table or function is obtained which relates focusing strengths of an objective lens 150 to the respective focusing distances of the objective lens 150. The objective lens 150 may be a part of a charged particle beam device 100 according to embodiments described herein. The focusing distances are distances from the objective lens where a sample surface is to be arranged in order to obtain a sharp image of the sample surface when exciting the objective lens with the corresponding focusing strength (e.g., with a corresponding focusing current FC).

Optionally, in box 710, the charged particle beam device 100 may be calibrated utilizing a calibration object arranged at a predetermined working distance WD from the objective lens. Optionally, in box 710, the working point of the charged particle beam device may be set such that aberration-reduced images can be obtained from a sample surface arranged at the predetermined working distance.

In box 720, a sample 10 to be inspected is arranged on a stage 20 of the charged particle beam device. The sample has a first surface region 11 that is arranged at an (initially unknown) first distance D1 from the objective lens 150 in the direction of the optical axis. A first focusing strength of the objective lens adapted to focus the charged particle beam on a first surface region is determined, e.g. by conducting an autofocusing process. Then, a difference between the first distance D1 and the predetermined working distance WD is calculated based on the determined first focusing strength and utilizing the table or function obtained in box 710.

In box 730, the distance between the first surface region 11 and the objective lens 150 is adjusted by moving the stage 20 by the difference calculated in box 720. Accordingly, the first surface region 11 is moved into a plane of focus that is arranged at the predetermined working distance WD from the objective lens. The first surface region 11 can then be inspected, e.g. for performing one or more of: defect review, metrology and inspection of features of the sample, and/or measurements, such as critical dimension measurements.

Figure 8:
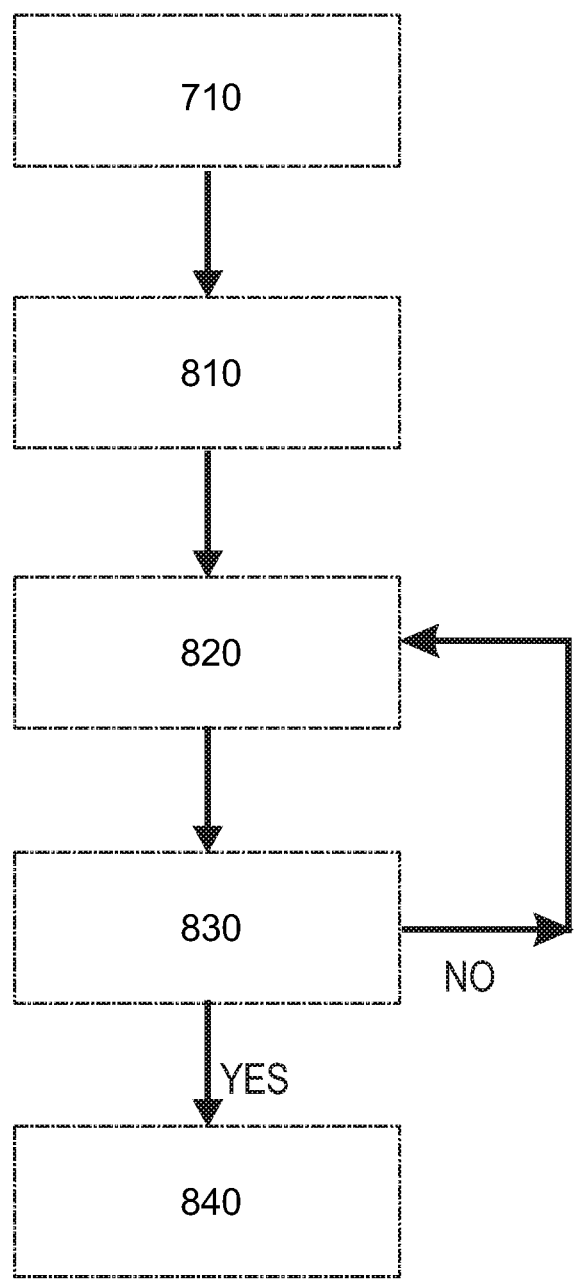
FIG. 8 is a flow diagram illustrating a method of inspecting a sample according to embodiments described herein.

FIG. 8 is a flow diagram for illustrating a method of inspecting a sample according to embodiments described herein.

In box 710, as already explained above, a table or function may be obtained which relates focusing strengths of an objective lens to the respective focusing distances FD of the objective lens 150.

In box 810, a sample 10 to be inspected is arranged on the stage 20 of the charged particle beam device. The sample has a first surface region 11 that is arranged at an (initially unknown) distance from the objective lens 150 in the direction of the optical axis. A focusing strength of the objective lens adapted to focus the charged particle beam on the first surface region is determined, e.g. by conducting an autofocusing process.

In box 820, a difference between the distance and a predetermined working distance WD is calculated based on the focusing strength determined in box 810 and utilizing the table or function obtained in box 710.

In box 830, the distance between the first surface region and the objective lens 150 is adjusted by moving the stage 20 by the difference calculated in box 820. Accordingly, the first surface region 11 is moved close to a plane of focus that is arranged at the predetermined working distance WD from the objective lens. However, the first surface region 11 may not yet be arranged exactly at the predetermined working distance, e.g. due to mechanical tolerances of a stage movement system. Accordingly, it may be checked whether the first surface region is now arranged close enough to the predetermined working distance WD.

In the case of a positive check result, the method proceeds with box 840 where the first surface region is inspected.

In the case of a negative check result, the method returns to box 820 where, again, the difference between the (already adjusted) distance and the predetermined working distance WD is calculated based on a second focusing strength adapted to focus the charged particle beam on the first surface region and utilizing the table or function obtained in box 710. In box 830, the stage is moved by said calculated difference such that the first surface region is brought yet closer to the predetermined working distance.

In box 830, said check can optionally be carried out by determining a second focusing strength of the objective lens adapted to focus the charged particle beam on the first surface region, and calculating whether a difference between the second focusing strength and a predetermined focusing strength is smaller than a predetermined threshold value.

The first surface region is inspected, e.g. for performing one or more of: defect review, metrology and inspection of features of the sample, and/or measurements, such as critical dimension measurements.

Methods described herein allow for (i) a real-time control of a distance between the column of a scanning electron microscope and a sample surface to be inspected. (ii) This control is on-axis and provides for a correction of the position of sample in the direction of the optical axis (A). Other technologies may measure an off-axis distance between the sample and the objective lens which may be less accurate. (iii) By correcting the position of the sample surface along the optical axis A, the accuracy of calibrations of nm/pixel can be maintained, and a robust method for maintaining the critical dimension (CD) control in metrology can be provided (especially for samples which span over areas in the order of several square meters). (iv) Methods described herein result in an enhanced CD accuracy for LV-SEMs, particularly for samples which are large in area and/or are not planar and/or are electrically floating (cannot be brought to a certain electric potential). (v) Accordingly, a real-time control of a distance between a sample and a scanning electron microscope for a LV-SEM is provided which in turn leads to an error minimization of metrology measurements to be performed.

Regular process control may be beneficial in the production of flat panels, displays, OLED devices such as OLED screens, TFT based substrates and other samples including a plurality of electronic or optoelectronic devices formed thereon. Process control may include regular monitoring, imaging and/or inspection of certain critical dimensions as well as defect review.

While the foregoing is directed to some embodiments, other and further embodiments may be devised without departing from the basic scope thereof, and the scope thereof is determined by the claims that follow.

The invention claimed is:

1. A method of inspecting a sample with a charged particle beam device, comprising:
arranging the sample on a stage;
determining a first focusing strength of an objective lens adapted to focus a charged particle beam on a first surface region of the sample that is arranged at a first distance from the objective lens in a direction of an optical axis;
calculating a difference between the first distance and a predetermined working distance based on a measured focusing current at the determined first focusing strength;
adjusting a distance between the first surface region and the objective lens by the calculated difference; and
inspecting the first surface region.

2. The method of claim 1, wherein the distance between the first surface region and the objective lens is adjusted by moving the stage by the calculated difference in the direction of the optical axis, wherein the stage is stationary while determining the first focusing strength and calculating the difference between the first distance and the predetermined working distance.

3. The method of claim 1, wherein the first focusing strength of the objective lens is determined by an autofocusing process.

4. The method of claim 3, wherein the autofocusing process comprises imaging the first surface region with varying focusing strengths of the objective lens and analyzing an image sharpness or an image contrast of obtained images.

5. The method of claim 1, wherein the difference is calculated based on the measured focusing current at the determined first focusing strength and using a previously obtained table or function which relates focusing currents of the objective lens to respective focusing distances of the objective lens.

6. The method of claim 1, wherein the distance between the first surface region and the objective lens is adjusted in an iterative process.

7. A method of inspecting a sample with a charged particle beam device, comprising:
arranging the sample on a stage;
determining a first focusing strength of an objective lens adapted to focus a charged particle beam on a first surface region of the sample that is arranged at a first distance from the objective lens in a direction of an optical axis;
calculating a difference between the first distance and a predetermined working distance based on the determined first focusing strength;
adjusting a distance between the first surface region and the objective lens by the calculated difference; and
inspecting the first surface region,
wherein after adjusting the distance between the first surface region and the objective lens by the calculated difference:
determining a second focusing strength of the objective lens adapted to focus the charged particle beam on the first surface region;
calculating whether a difference between the second focusing strength and a predetermined focusing strength is smaller than a predetermined threshold value, and continuing with the inspection of the first surface region, if the difference between the second focusing strength and the predetermined focusing strength is smaller than the predetermined threshold value.

8. The method of claim 7, further comprising pre-specifying a measurement accuracy; and
determining the predetermined threshold value such that, in the case of a positive calculation result, the first surface region is arranged close enough to the predetermined working distance for being inspected with a measurement accuracy better than or equal to the pre-specified measurement accuracy.

9. The method of claim 1, further comprising: previously calibrating the charged particle beam device by:
arranging a scan object with one or more known lateral dimensions at the predetermined working distance; and
determining a relation between a scan current of a scan deflector and at least one lateral dimension of the scan object.

10. The method of claim 1, wherein the charged particle beam impinges on the sample with a landing energy of 5 keV or less.

11. The method of claim 1, wherein a plurality of surface regions of the sample are subsequently inspected, the inspection of each of the plurality of surface regions comprising:
determining a respective focusing strength adapted to focus the charged particle beam on the respective surface region which is arranged at a respective distance from the objective lens;

calculating a difference between the respective distance and the predetermined working distance based on the respective focusing strength; and adjusting a distance between the respective surface region and the objective lens by moving the stage by the calculated difference in the direction of the optical axis.

12. The method of claim 1, wherein the first surface region and a second surface region of the sample laterally spaced-apart from the first surface region are located at different levels in the direction of the optical axis, the method comprising:

successively inspecting the first surface region and the second surface region at the predetermined working distance by providing a real-time control of a position of the stage along the optical axis.

13. The method of claim 1, wherein the sample comprises a large-area substrate for display manufacturing having a surface area of 1 $m^2$ or more.

14. A charged particle beam device for inspecting a sample, comprising:

a stage for arranging a sample to be inspected;

an objective lens configured to focus a charged particle beam propagating along an optical axis on the sample;

a processing unit configured to determine a first focusing strength of the objective lens adapted to focus the charged particle beam on a first surface region of the sample that is arranged at a first distance from the objective lens in a direction of an optical axis;

a calculation unit configured to calculate a difference between the first distance and a predetermined working distance based on a measured focusing current at the determined first focusing strength; and an adjusting unit configured to adjust a distance between the first surface region and the objective lens by the calculated difference.

15. The charged particle beam device of claim 14, wherein the adjusting unit comprises a stage motion controller configured to move the stage in the direction of the optical axis.

16. The charged particle beam device of claim 14, wherein the processing unit comprises an image acquisition and analyzing unit, particularly an autofocusing device.

17. The charged particle beam device of claim 14, wherein the calculation unit comprises a memory, wherein a table or function which relates focusing strengths of the objective lens to respective focusing distances of the objective lens is stored in the memory.

18. The charged particle beam device of claim 14, wherein the objective lens comprises a retarding field component configured to decelerate the charged particle beam to a landing energy of 5 keV or less.

19. The charged particle beam device of claim 14, wherein the stage is configured for supporting a large-area substrate for display manufacturing having a size of 1 $m^2$ or more.

* * * * *